United States Patent
Holmberg

(10) Patent No.: US 12,239,849 B2
(45) Date of Patent: Mar. 4, 2025

(54) CHECKING QUALITY OF A TREATMENT PLAN

(71) Applicant: RaySearch Laboratories AB, Stockholm (SE)

(72) Inventor: Rickard Holmberg, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 379 days.

(21) Appl. No.: 17/786,420

(22) PCT Filed: Dec. 9, 2020

(86) PCT No.: PCT/EP2020/085227
§ 371 (c)(1),
(2) Date: Jun. 16, 2022

(87) PCT Pub. No.: WO2021/122203
PCT Pub. Date: Jun. 24, 2021

(65) Prior Publication Data
US 2023/0032956 A1    Feb. 2, 2023

(30) Foreign Application Priority Data
Dec. 18, 2019   (EP) .................................... 19217514

(51) Int. Cl.
*A61N 5/10*    (2006.01)

(52) U.S. Cl.
CPC .......... *A61N 5/1038* (2013.01); *A61N 5/1071* (2013.01)

(58) Field of Classification Search
CPC .......................... A61N 5/1038; A61N 5/1071
See application file for complete search history.

(56) References Cited

U.S. PATENT DOCUMENTS

2016/0140300 A1* 5/2016 Purdie .................. G16H 20/40
                                                                  705/2
2019/0262077 A1   8/2019 Isola et al.

FOREIGN PATENT DOCUMENTS

CN    105825073 A    8/2016
CN    109771843 A    5/2019
(Continued)

OTHER PUBLICATIONS

European Communication pursuant to Article 94(3) EPC issued May 28, 2024 in Application No. 19217514.9.

*Primary Examiner* — Nicole M Ippolito
*Assistant Examiner* — Hanway Chang
(74) *Attorney, Agent, or Firm* — Faegre Drinker Biddle & Reath LLP

(57) ABSTRACT

It is provided a method for checking quality of a treatment plan, wherein a treatment plan specifies a distribution of radiation to thereby provide radiation to a planning target volume. The method is performed by a quality assurance device and comprises the steps of: obtaining a treatment plan and a corresponding first dose, the treatment plan having been calculated in a treatment planning system, the first dose being a predicted dose to be deposited in the patient using the treatment plan; initiating a calculation of a secondary dose, being a dose deposited by the treatment plan, using a secondary dose calculation algorithm; repeatedly calculating a confidence interval of a comparative statistical measurement by comparing the first dose and the secondary dose over a defined geometric volume; and interrupting the calculation of the secondary dose when the confidence interval is better than at least one predefined criterion.

13 Claims, 2 Drawing Sheets

(56) References Cited

FOREIGN PATENT DOCUMENTS

| | | | |
|---|---|---|---|
| CN | 109890461 | A | 6/2019 |
| CN | 110580580 | A | 12/2019 |
| DE | 10 2012 219 709 | A1 | 4/2014 |
| EP | 3 103 521 | A1 | 12/2016 |
| JP | 2017-536190 | A | 12/2017 |
| JP | 2019-526380 | A | 9/2019 |
| WO | WO-2016/088075 | A1 | 6/2016 |
| WO | WO-2018/048575 | A1 | 3/2018 |
| WO | WO-2018/077709 | A1 | 5/2018 |
| WO | WO-2018/185063 | A1 | 10/2018 |
| WO | WO-2018/235649 | A1 | 12/2018 |
| WO | WO-2021/090063 | A1 | 5/2021 |

* cited by examiner

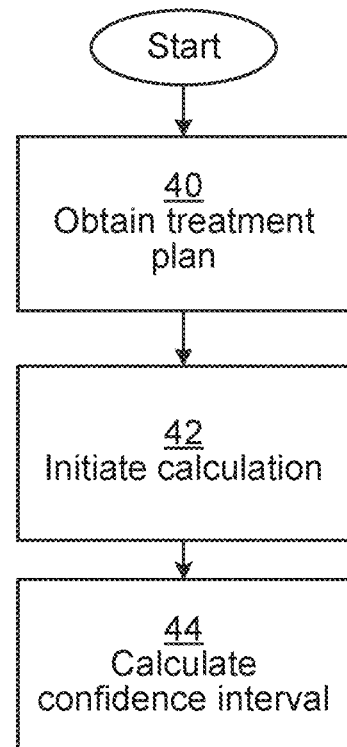
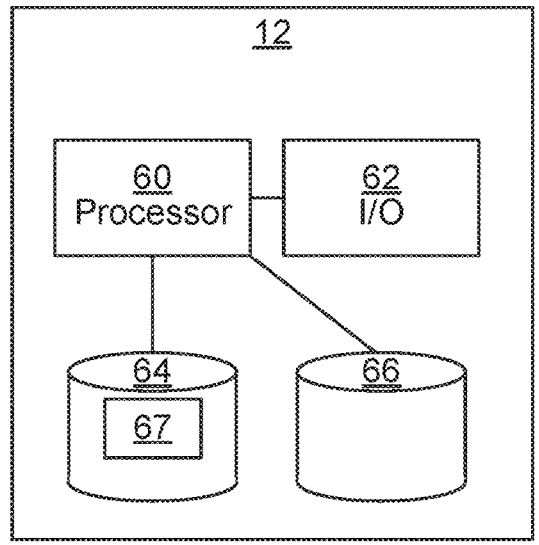
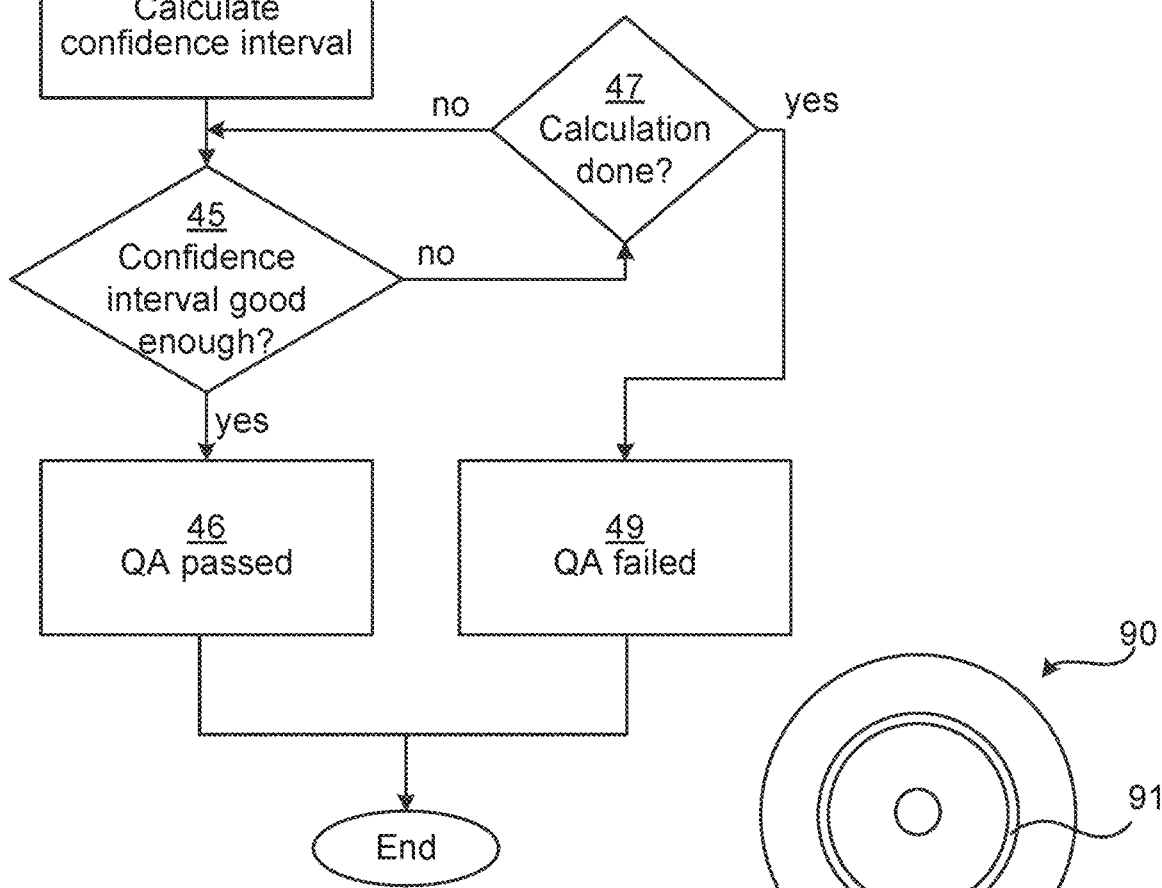
Fig. 3
Fig. 4
Fig. 5

CHECKING QUALITY OF A TREATMENT PLAN

TECHNICAL FIELD

The present disclosure relates to the field of radiotherapy and in particular to checking quality of a treatment plan for radiotherapy.

BACKGROUND

In radiotherapy, a target volume is irradiated by one or several therapeutic beams. Various types of therapeutic beams can be used, e.g. photon, electron and ion beams. The target volume can represent a cancer tumor. The therapeutic beam penetrates tissue and delivers an absorbed radiation dose to kill the tumor cells.

A treatment planning system is used to determine a treatment plan which defines how a radiation delivery system is to deliver the dose. When a treatment plan is determined, quality assurance can be used to ensure the treatment plan is of sufficient quality.

WO 2018/048575 A1 discloses a system and method for learning models of radiotherapy treatment plans to predict radiotherapy dose distributions. WO 2018/077709 A1 discloses a graphical user interface for iterative treatment planning. EP 3 103 541 A1 discloses improvements in dosimetry techniques for radiotherapy.

The quality assurance performed in the prior art is very time consuming and can take hours to complete. This is not practically feasible e.g. if a treatment plan is determined based on a patient geometry on the day of treatment.

SUMMARY

One object is to provide quality assurance of treatment plan in a more time efficient manner.

According to a first aspect, it is provided a method for checking quality of a treatment plan, wherein a treatment plan specifies a distribution of radiation to thereby provide radiation to a planning target volume. The method is performed by a quality assurance device and comprises the steps of: obtaining a treatment plan and a corresponding first dose, the treatment plan having been calculated in a treatment planning system, the first dose being a predicted dose to be deposited in the patient using the treatment plan; initiating a calculation of a secondary dose, being a dose deposited by the treatment plan, using a secondary dose calculation algorithm; repeatedly calculating a confidence interval of a comparative statistical measurement by comparing the first dose and the secondary dose over a defined geometric volume; and interrupting the calculation of the secondary dose when the confidence interval is better than at least one predefined criterion, in which case the treatment plan is considered to pass quality assurance.

Each voxel in the secondary dose may comprise estimates of a current confidence interval for the voxel.

The defined geometric volume may be the planning target volume.

The defined geometric volume may be an organ at risk.

The defined geometric volume may cover the planning target volume and an organ at risk.

The step of calculating the confidence interval of the comparative statistical measurement may be based on available confidence intervals for voxels in the secondary dose, and on a spread of possible secondary dose.

The comparative statistical measurement may be based on calculating a similarity by accumulating difference measurements between corresponding voxels in the first dose and the second dose.

The comparative statistical measurement may be based on calculating a similarity by finding a difference between a third value and a fourth value, wherein the third value is obtained by accumulating dose values of the first dose in all voxels in the defined geometric volume, and the fourth value is obtained by accumulating dose values of the second dose in all voxels of the defined geometric volume.

According to a second aspect, it is provided a quality assurance device for checking quality of a treatment plan, wherein a treatment plan specifies a distribution of radiation to thereby provide radiation to a planning target volume. The quality assurance device comprises: a processor; and a memory storing instructions that, when executed by the processor, cause the quality assurance device to: obtain a treatment plan and a corresponding first dose, the treatment plan having been calculated in a treatment planning system, the first dose being a predicted dose to be deposited in the patient using the treatment plan; initiate a calculation of a secondary dose, being a dose deposited by the treatment plan, using a secondary dose calculation algorithm; repeatedly calculate a confidence interval of a comparative statistical measurement by comparing the first dose and the secondary dose over a defined geometric volume; and interrupt the calculation of the secondary dose when the confidence interval is better than at least one predefined criterion, in which case the treatment plan is considered to pass quality assurance.

Each voxel in the secondary dose may comprise estimates of a current confidence interval for the voxel.

The defined geometric volume may be the planning target volume.

The defined geometric volume may be an organ at risk.

The defined geometric volume may cover the planning target volume and an organ at risk.

According to a third aspect, it is provided a computer program for checking quality of a treatment plan, wherein a treatment plan specifies a distribution of radiation to thereby provide radiation to a planning target volume. The computer program comprises computer program code which, when run on a quality assurance device causes the quality assurance device to: obtain a treatment plan and a corresponding first dose, the treatment plan having been calculated in a treatment planning system, the first dose being a predicted dose to be deposited in the patient using the treatment plan; initiate a calculation of a secondary dose, being a dose deposited by the treatment plan, using a secondary dose calculation algorithm; repeatedly calculate a confidence interval of a comparative statistical measurement by comparing the first dose and the secondary dose over a defined geometric volume; and interrupt the calculation of the secondary dose when the confidence interval is better than at least one predefined criterion, in which case the treatment plan is considered to pass quality assurance.

According to a fourth aspect, it is provided a computer program product comprising a computer program according to the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, in which:

FIG. 3 is a flow chart illustrating methods for checking quality of a treatment plan;

FIG. 4 is a schematic diagram illustrating components of the quality assurance device of FIG. 1; and FIG. 5 shows one example of a computer program product comprising computer readable means.

DETAILED DESCRIPTION

The aspects of the present disclosure will now be described more fully hereinafter with reference to the accompanying drawings, in which certain embodiments of the invention are shown. These aspects may, however, be embodied in many different forms and should not be construed as limiting; rather, these embodiments are provided by way of example so that this disclosure will be thorough and complete, and to fully convey the scope of all aspects of invention to those skilled in the art. Like numbers refer to like elements throughout the description.

Figure 1:
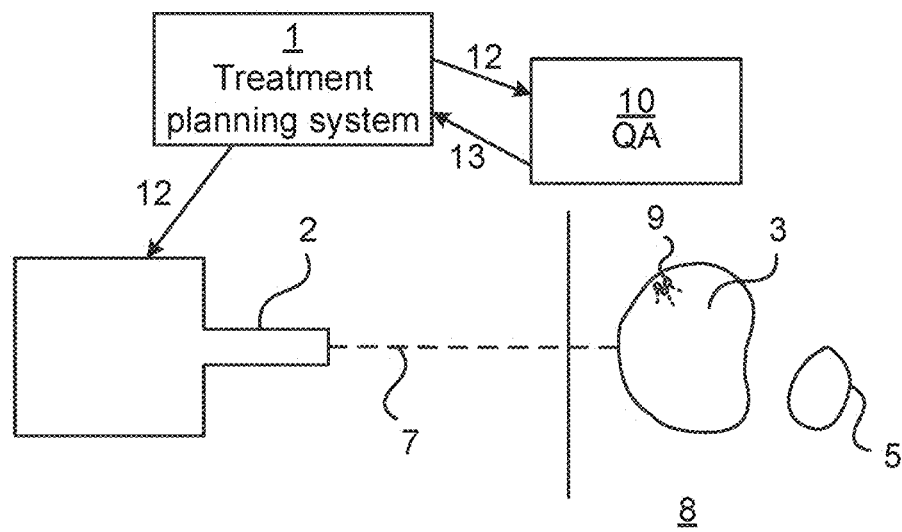
FIG. 1 is a schematic drawing illustrating an environment in which embodiments presented herein can be applied.

FIG. 1 is a schematic diagram illustrating an environment in which embodiments presented herein can be applied. A treatment planning system 1 determines a distribution radiation for radiation therapy, in the form of a treatment plan 12. The treatment plan 12 is provided to a quality assurance device 10 which evaluates the treatment plan 12 as described in more detail below. It is to be noted that while the quality assurance device 10 is here shown as external to the treatment planning system 1, the quality assurance device 10 may also be internal within the treatment planning system 1.

The result 13 of the quality assurance is provided from the quality assurance device 10 to the treatment planning system 1. If the result 13 is positive, the treatment planning system 1 proceeds and provides a corresponding treatment plan 12 to a radiation delivery system 2. Based on the treatment plan 12, the radiation delivery system 2 generates a beam 7 for providing radiation to a target volume 3 of a patient 8, while avoiding radiation to an organ at risk 5.

The way in which the radiation delivery system 2 generates the beam and delivers the dose differs depends on the treatment modality (such as photons, electrons, or ions) as is well known in the industry per se. However, the common goal is to deliver a dose to the target volume (i.e. the tumor) 3 that is as close as possible to a prescribed dose while minimizing the dose to organs at risk 5 such as bladder, brain and rectum depending on where the tumor is located.

Figure 2A:
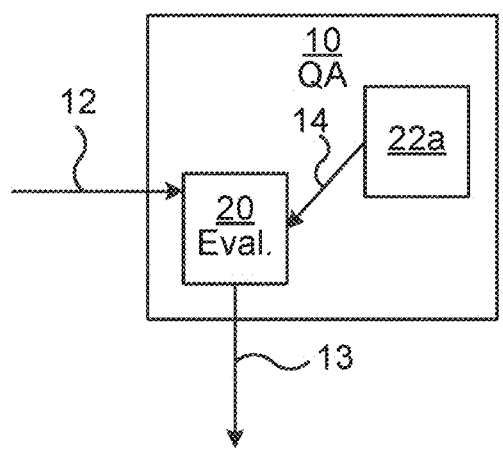
FIG. 2A-B are schematic drawings illustrating two embodiments of the quality assurance device.
Figure 2B:
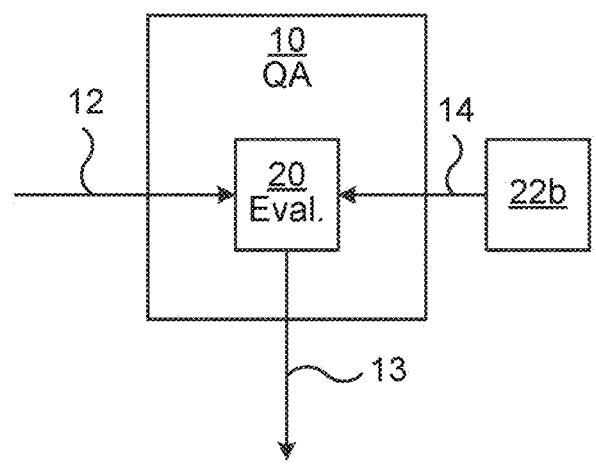

FIG. 2A-B are schematic drawings illustrating two embodiments of the quality assurance device 10. First, the embodiment of FIG. 2A will be described.

An evaluator module 20 evaluates the treatment plan 12. The evaluation is based on evaluating the treatment plan 12 (from the treatment planning system) and the dose of this plan, here denoted a first dose. The first dose is compared to a secondary dose 14, which is calculated by a dose calculator 22a. If the evaluation is positive, the evaluator 20 sends the result 13 to the treatment planning system and the dose calculator ends its calculation of the secondary dose. Also, if the calculation of the secondary dose 14 has reached an end condition and the evaluator has not yet determined a positive evaluation, the result 13 is negative. In FIG. 2A, the dose calculator 22a is a dose calculator which is internal to the quality assurance device 10.

Looking now to FIG. 2B, in this embodiment, the dose calculator 22b is external to the quality assurance device 10.

FIG. 3 is a flow chart illustrating methods for checking quality of a treatment plan. As explained above, the treatment plan specifies a distribution of radiation to thereby provide radiation to a planning target volume. The methods are performed by the quality assurance device.

In an obtain treatment plan step 40, the quality assurance device obtains a treatment plan and a corresponding first dose. The first dose is defined by the treatment plan. The treatment plan has been calculated in a treatment planning system and can be obtained from the treatment planning system. The first dose is a predicted dose to be deposited in the patient using the treatment plan. It is the treatment plan that is evaluated with regards to quality assurance.

In an initiate calculation step 42, the quality assurance device initiates a calculation of a secondary dose, calculated by the dose calculator. The secondary dose is a dose defined to be deposited by the treatment plan, which can be calculated per voxel. The secondary dose is calculated using a secondary dose calculation algorithm. Each voxel in the secondary dose can comprise estimates of a current confidence interval for the voxel. The secondary dose calculation algorithm differs from the dose calculation algorithm of the treatment plan which calculates the first dose. Otherwise, any comparison of the first and second doses would be irrelevant since they would amount to the same. For instance, the first dose calculation algorithm can be based on an analytical model of whole dose is deposited in tissue, while the second dose algorithm can be based on a Monte Carlo-simulation of particle transport. It is to be noted that the calculation of the secondary dose can continue in parallel to all other steps of this method, until the calculation of the secondary dose is interrupted.

In a calculate confidence interval step 44, the quality assurance device repeatedly calculates a confidence interval of a comparative statistical measurement by comparing the first dose and the secondary dose over a defined geometric volume.

The defined geometric volume can be any suitable geometric volume for which this comparison is made. For instance, the defined geometric volume can be the planning target volume, an organ at risk or a volume that covers the planning target volume and an organ at risk. The defined geometric volume can also be the whole patient body.

The calculation of the confidence interval of the comparative statistical measurement can be based on available confidence intervals for voxels in the secondary dose, and on a spread of possible secondary dose, e.g. a spread of dose in each voxel from a Monte Carlo-simulation.

The comparative statistical measurement can e.g. be based on standard deviation of the second dose.

In one embodiment, the confidence interval is calculated according to:

$$CI=[S(TP,D_{ID}+\sigma_{ID}(t)),S(TP,D_{ID}-\sigma_{ID}(t))] \qquad (1)$$

where CI denotes the confidence interval, S is a similarity operation (e.g. as exemplified below), TP is the treatment plan, DID is the second dose and $\sigma_{ID}$ (t) is the standard deviation of the second dose, which depends on time since the secondary dose is calculated and evaluated successively. Expressed in words, the confidence interval is then the interval between a first similarity and a second similarity. The first similarity is a similarity between the first dose (of the treatment plan) and a sum of the second dose and its standard deviation. The second similarity is a similarity between the first dose and the second dose minus its standard deviation.

In one embodiment, the similarity between two doses is calculated according to:

$$S(D1,D2)=\iiint_v (D1-D2)^2 d\vec{x} \qquad (2)$$

where S is the similarity, D1 is a first dose, D2 is a second dose, v is the defined geometric volume, and $\vec{x}$ is a voxel. Expressed in words, the similarity can be calculated by accumulating difference measurements between corresponding voxels in the first dose and the second dose.

In one embodiment, the similarity is calculated according to:

$$S(D1, D2) = \frac{\left(\iiint_v D1 d\vec{x}\right)-\left(\iiint_v D2 d\vec{x}\right)}{\iiint_v d\vec{x}} \qquad (3)$$

Expressed in words, the similarity can be based on finding a difference between a third value and a fourth value, wherein the third value is obtained by accumulating dose values of the first dose in all voxels in the defined geometric volume, and the fourth value is obtained by accumulating dose values of the second dose in all voxels of the defined geometric volume. This difference is then normalised by dividing it by the volume of the geometric volume.

In a conditional confidence interval good enough step 45, the quality assurance device determines if the confidence interval calculated in step 44 is good enough. This can be determined by comparing the calculated confidence interval with at least one predefined criterion. The at least one criterion can be one or more threshold values. In one embodiment, the at least one predefined criterion is a single threshold value. For instance, the predefined criterion can be defined such that the confidence interval is considered to be good enough when it is less than a certain percentage. This comparison can be made for each voxel of the defined geometric volume. In this case, all voxels need to be sufficiently good for the quality assurance to pass.

If the confidence interval is good enough, the method proceeds to a QA passed step 46. Otherwise, the method proceeds to a conditional calculation done step 47.

In the QA passed step 46, the quality assurance device interrupts the calculation of the secondary dose. In this step, the treatment plan is considered to pass quality assurance.

In the conditional calculation done step 47, the quality assurance device determines whether the calculation of the secondary dose is done. If this is the case, the method proceeds to a QA failed step 49 (since the confidence interval cannot be good enough for the method to be in step 47). If the calculation of the secondary dose is not done, the method returns to the conditional confidence interval good enough step 45, optionally after an idle period (not shown).

In the QA failed step 49, the quality assurance device determines that the quality assurance has failed, since this step can only be performed when the confidence interval is not good enough and when the calculation of the secondary dose is done.

Using embodiments presented herein, as soon as the secondary dose indicates that the quality is sufficiently good, the quality assurance is affirmed, and no more time needs to be spent on further dose calculations for the quality assurance. Unlike the prior art, where each voxel needed to be sufficiently good for quality assurance to pass, this method is based on comparing of a whole defined volume. This leads to a significantly quicker quality assurance than the prior art. In particular, this quality assurance can be applied e.g. for online adaptive treatment plans, which can be used to determine a treatment plan on a patient geometry on the day of treatment, since patient geometry can differ significantly, for instance due to bladder state and stomach state.

FIG. 4 is a schematic diagram illustrating components of the quality assurance device 10 of FIG. 1. A processor 60 is provided using any combination of one or more of a suitable central processing unit (CPU), multiprocessor, microcontroller, digital signal processor (DSP), etc., capable of executing software instructions 67 stored in a memory 64, which can thus be a computer program product. The processor 60 could alternatively be implemented using an application specific integrated circuit (ASIC), field programmable gate array (FPGA), etc. The processor 60 can be configured to execute the method described with reference to FIG. 2 above.

The memory 64 can be any combination of random-access memory (RAM) and/or read-only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of RAM and/or ROM.

The quality assurance device 10 further comprises an I/O interface 62 for communicating with external and/or internal entities. Optionally, the I/O interface 62 also includes a user interface.

Other components of the quality assurance device 10 are omitted in order not to obscure the concepts presented herein.

FIG. 5 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 3. While the computer program 91 is here schematically shown as a track on the depicted optical disk, the computer program can be stored in any way which is suitable for the computer program product, such as a removable solid-state memory, e.g. a Universal Serial Bus (USB) drive.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims. Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for checking quality of a treatment plan, wherein a treatment plan specifies a distribution of radiation to thereby provide radiation to a planning target volume, the method being performed by a quality assurance device and comprising the steps of:
   obtaining a treatment plan and a corresponding first dose, the treatment plan having been calculated in a treatment planning system, the first dose being a predicted dose to be deposited in the patient using the treatment plan;
   initiating a successive calculation of a secondary dose, being a dose deposited by the treatment plan, using a secondary dose calculation algorithm;
   while the successive calculation of the secondary dose continues, repeatedly calculating a confidence interval of a comparative statistical measurement by comparing the first dose and the secondary dose over a defined geometric volume; and
   interrupting the calculation of the secondary dose when the current confidence interval is better than at least one predefined criterion, in which case the treatment plan is considered to pass quality assurance.

2. The method according to claim 1, wherein, for each voxels, the secondary dose comprises estimates of a current confidence interval for the voxel.

3. The method according to claim 1, wherein the defined geometric volume is the planning target volume.

4. The method according to claim 1, wherein the defined geometric volume is an organ at risk.

5. The method according to claim 1, wherein the step of calculating the confidence interval of the comparative statistical measurement is based on available confidence intervals for voxels in the secondary dose, and on a spread of possible secondary dose.

6. The method according to claim 5, wherein the comparative statistical measurement is based on calculating a similarity by accumulating difference measurements between corresponding voxels in the first dose and the second dose.

7. The method according to claim 5, wherein the comparative statistical measurement is based on calculating a similarity by finding a difference between a third value and a fourth value, wherein the third value is obtained by accumulating dose values of the first dose in all voxels in the defined geometric volume, and the fourth value is obtained by accumulating dose values of the second dose in all voxels of the defined geometric volume.

8. A quality assurance device for checking quality of a treatment plan, wherein a treatment plan specifies a distribution of radiation to thereby provide radiation to a planning target volume, the quality assurance device comprising:
   a processor; and
   a memory storing instructions that, when executed by the processor, cause the quality assurance device to:
   obtain a treatment plan and a corresponding first dose, the treatment plan having been calculated in a treatment planning system, the first dose being a predicted dose to be deposited in the patient using the treatment plan;
   initiate a successive calculation of a secondary dose, being a dose deposited by the treatment plan, using a secondary dose calculation algorithm;
   while the successive calculation of the secondary dose continues, repeatedly calculate a current confidence interval of a comparative statistical measurement by comparing the first dose and the secondary dose over a defined geometric volume; and
   interrupt the calculation of the secondary dose when the current confidence interval is better than at least one predefined criterion, in which case the treatment plan is considered to pass quality assurance.

9. The quality assurance device according to claim 8, wherein, for each voxel, the secondary dose comprises estimates of a current confidence interval for the voxel.

10. The quality assurance device according to claim 8, wherein the defined geometric volume is the planning target volume.

11. The quality assurance device according to claim 8, wherein the defined geometric volume is an organ at risk.

12. A computer program for checking quality of a treatment plan, wherein a treatment plan specifies a distribution of radiation to thereby provide radiation to a planning target volume, the computer program comprising computer program code which, when run on a quality assurance device causes the quality assurance device to:
   obtain a treatment plan and a corresponding first dose, the treatment plan having been calculated in a treatment planning system, the first dose being a predicted dose to be deposited in the patient using the treatment plan;
   initiate a successive calculation of a secondary dose, being a dose deposited by the treatment plan, using a secondary dose calculation algorithm;
   while the successive calculation of the secondary dose continues, repeatedly calculate a current confidence interval of a comparative statistical measurement by comparing the first dose and the secondary dose over a defined geometric volume; and
   interrupt the calculation of the secondary dose when the current confidence interval is better than at least one predefined criterion, in which case the treatment plan is considered to pass quality assurance.

13. A computer program product comprising a computer program according to claim 12 and a computer readable means on which the computer program is stored.

* * * * *